United States Patent [19]

Yamada

[11] Patent Number: 4,679,921
[45] Date of Patent: Jul. 14, 1987

[54] APPARATUS FOR EYE EXAMINATION
[75] Inventor: Kenji Yamada, Narashino, Japan
[73] Assignee: Nippon Kogaku K. K., Tokyo, Japan
[21] Appl. No.: 736,072
[22] Filed: May 20, 1985
[30] Foreign Application Priority Data May 26, 1984 [JP] Japan .................. 59-107308

[51] Int. Cl.$^4$ .......................... A61B 3/02; A61B 3/10
[52] U.S. Cl. .................... 351/222; 351/205; 351/211; 351/241
[58] Field of Search ............... 351/205, 206, 211, 212, 351/241, 235, 246, 234, 222

[56]  References Cited
U.S. PATENT DOCUMENTS 3,664,631  5/1972  Guyton ................................. 351/241
4,185,896  1/1980  Buhler .................................. 351/234
4,248,506  2/1981  Takahashi ............................ 351/207

Primary Examiner—Rodney B. Bovernick
Assistant Examiner—D. M. Dzierzynski
Attorney, Agent, or Firm—Shapiro and Shapiro

[57]  ABSTRACT

An eye-examining apparatus comprises a first positive lens unit, a negative lens unit, a second positive lens unit, a third positive lens unit and a target mark arranged in the named order from the side of the examined eye. The third positive lens unit is mounted movably along the optical axis. Between the first and second positive lens units there is interposed on astigmatic system rotatable about the optical axis. The negative lens unit, the second positive lens unit and the third positive lens unit are so arranged as to form an image of the mark at a position near the focal point on the target mark side of the first lens unit. The focal point on the examined eye of the composite system composed of the negative lens unit, the second positive lens unit and the third positive lens unit is approximately coincident with the position conjugate with the pupil of the examined eye relative to the first positive lens unit. The diopter of the apparatus is changed by moving the third positive lens unit and the change of the axis and degree of astigmatism are achieved by rotating the astigmatism system.

7 Claims, 2 Drawing Figures

F I G. 1
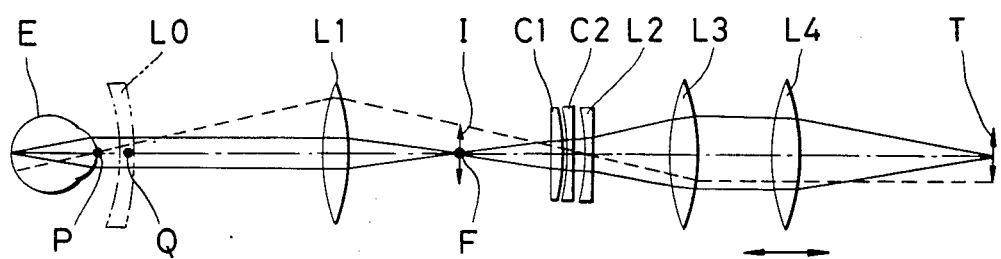
F I G. 2
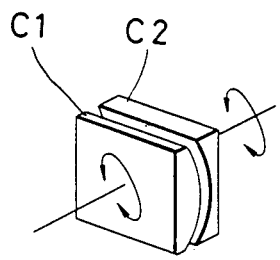

APPARATUS FOR EYE EXAMINATION

BACKGROUND OF THE INVENTION

1. Field of the Invention

The present invention relates to apparatus for the subjective examination of eye refractive power.

2. Description of the Prior Art

In order to examine eye refractive power there has conventionally been used such apparatus which comprises two boxes containing therein a number of lenses having different refractive powers. The two boxes which are to be placed in front of the right and left eyes to be examined, have each a window through which the examinee looks at a mark through one of the lenses contained in the boxes. With this apparatus, the eye examination is conducted in the following manner:

The examiner sets the apparatus immediately before the eyes to be examined and lets the examinee look at a mark through a lens selected from the lenses contained in the boxes. The mark is at a position, for example, 5 meters distant from the apparatus. The examiner changes the lens from one to another while asking the examinee whether he can view the mark well or not until the examiner finds out the lens through which the examinee can view the mark best. The examiner determines the refractive power of the examined eye from the refractive power of the lens.

The conventional eye examining apparatus has some important drawbacks. Since the apparatus contains many lenses therein, it is very complicated in construction and expensive. In addition, it needs a relatively wide room for conducting the examination because the mark has to be set at a distant point from the apparatus. Thus, the place available for the eye examination has been limited.

SUMMARY OF THE INVENTION

Accordingly it is the object of the present invention to provide an eye-examining apparatus which is simple in construction and allows the eye examination to be conducted anywhere.

The eye-examining apparatus according to the invention is of the type with which the eye refractive power is examined by letting the examined eye look at a projection image of a test mark. The apparatus comprises a first positive lens unit, a negative lens unit, a second positive lens unit, a third positive lens unit and a target mark arranged in the named order from the side of the examined eye. The third positive lens unit is mounted movably along the optical axis. Further, between the first and second positive lens units there is interposed an astigmatic system rotatable about the optical axis. The negative lens unit, the second positive lens unit and the third positive lens unit are so arranged as to form an image of the mark at a position near the focal point on the target mark side of the first lens unit.

The focal point on the examined eye of the composite system composed of the negative lens unit, the second positive lens unit and the third positive lens unit is approximately coincident with the position conjugate with the pupil of the examined eye relative to the first positive lens unit. The diopter (reciprocal of focal length) of the apparatus is changed by moving the third positive lens unit and the change of the axis and degree of astigmatism are achieved by rotating the astigmatic system.

Other objects, features and advantages of the invention will appear more fully from the following description taken in connection with the accompanying drawings.

BRIEF DESCRIPTION OF THE DRAWINGS

FIG. 1 schematically shows an embodiment of the eye-examining apparatus according to the invention; and FIG. 2 is a perspective view of a cylindrical lens member for the examination of astigmatism used in the invention.

DESCRIPTION OF THE PREFERRED EMBODIMENTS

Referring to FIG. 1 showing an embodiment of the invention, E denotes an eye to be examined and T denotes a target mark. Arranged from the side of the examined eye E are a first positive lens unit L1 whose focal point is designated by F, an astigmatic system C1, C2, a negative lens unit L2, a second positive lens unit L3 and a third positive lens unit L3 before the target T. The target T is illuminated by an illumination system not shown and an image I of the target is projected on the focal point F of the first positive lens unit L1 through the negative lens unit L2. The astigmatic system disposed between the focal point F and the negative lens unit L2 is used for the detection of astigmatism and comprises a positive cylindrical lens C1 and a negative cylindrical lens C2. As seen best from FIG. 2, the two cylindrical lenses C1 and C2 of the astigmatic system are rotatable about the optical axis. The astigmatic system C1, C2 are disposed approximately conjugated with the imaginary spectacles position Q relative to the first positive lens unit L1. The imaginary spectacles position Q corresponds to the position at which the spectacles suggested by phantom line Lo would lie if the examinee (whose eye is E) wore the spectacles Lo. Of course, during the examination of the eye E, the spectacles Lo are absent.

The negative lens unit L2, the second positive lens unit L3 and the third positive lens unit L4 constitute a composite system whose focal point on the subject eye side is approximately coincident with the position conjugate with the pupil P of the eye relative to the first positive lens unit. In FIG. 1, the light ray represented by the solid line shows the conjugated relation between the target T and the fundus of the examined eye E. The light ray represented by the dotted line shows the conjugated relation with the pupil P.

The third positive lens unit L4 is movable along the optical axis to change the diopter of the optical system of the eye-examining apparatus. The two cylindrical lenses C1 and C2 are rotatable relative to each other to change the degree of astigmatism. They are rotatable also together to change the axis of astigmatism.

When the position of the target image I viewed by the eye E is just coincident with the focal point F of the first positive lens unit L1, the latter forms a virtual image of the target image at infinity. In this position, the diopter is 0. This position corresponds to the position shown in FIG. 1. In case that the examined eye is shortsighted, the third positive lens unit L4 is moved in the direction toward the target T along the optical axis. Thereby the target image I moves toward the eye side from the focal point F of the first positive lens unit so that the diopter is changed to a negative diopter value. If the eye E is long-sighted, the third positive lens unit L4 is moved in the direction away from the target T. Thereby the target image I moves toward the target T from the focal point F so that the diopter is changed to a positive diopter value.

The two cylindrical lenses C1 and C2 have the same astigmatic degree in absolute value but opposite in sign. When the axes of the two cylindrical lenses are parallel with each other, their refractive powers cancel out each other and, therefore, the astigmatic degree of the optical system of the apparatus is set to 0. The optical system of the apparatus has the maximum astigmatic degree when the axes of the two cylindrical lenses are perpendicular to each other. The value of the maximum astigmatic degree is two times larger than that of the single cylindrical lens C1 or C2. In this manner it is possible to continuously change the astigmatic degree from 0 to the maximum by changing the relative position between the cylindrical lenses C1 and C2 from parallel to perpendicular and to set the astigmatic degree to any intermediate value between 0 and the maximum. Further it is possible to set the astigmatic axis to any angle while keeping the astigmatic degree at a constant value by rotating the two cylindrical lenses C1 and C2 together in the same direction while keeping the angle between the two lens axes constant.

With the above construction of the apparatus, the diopter can be corrected by moving the third positive lens unit L4. The astigmatic degree as well as the astigmatic axis can be corrected by rotating the cylindrical lenses C1 and C2.

The characteristic value of the refractive power of the examined eye can be determined from the moved distance of the third positive lens unit and the rotation angle of the respective cylindrical lenses.

Like the prior art eye examination apparatus, the apparatus according to the invention can be used also to measure the sight of the examined eye after the correction provided by adjustment of the lens L4 and the cylindrical lenses C1 and C2 (hereinafter this sight is referred to as the corrected sight). To this end, a set of patterns having different sizes are prepared as the target mark. The examiner lets the examinee look at the target while changing the target pattern from large to small successively. The corrected sight of the examined eye can be determined from the size of the smallest pattern which the eye can distinguish. For this purpose, it is desirable that the apparent size of the target should remain unchanged even when the diopter is changed by the movement of the third positive lens unit L4. The apparatus according to the invention meets this desire. In the above-shown embodiment of the invention, the magnification change of the target image with the moving of the third positive lens unit is practically negligibly small. This is evident from the disclosure in the specification of U.S. Pat. No. 4,248,506. From the optical relation between the fundus of the examined eye E and the target T in the apparatus shown in FIG. 1, the image of the eye fundus may be considered to be formed on the target T as in the case of the retinal camera disclosed in the above-referred U.S. Pat. No. 4,248,506 specification. And the image height y of the eye fundus image on the target T is given by $$y = \frac{f_1 \cdot f_3 \cdot \tan\theta}{f_2}\left(1 + \frac{x^2}{f_3^2}\right)$$

wherein,
$f_1$ is the focal length of the first positive lens unit L1,
$f_2$ is the composite focal length resulting from the negative lens unit L2 and the second positive lens unit L3,
$f_3$ is the focal length of the third positive lens unit L4
x is the moved distance of the third positive lens unit L4, and
$\theta$ is the half angle of view of the first positive lens unit.

Since the moved distance x of the third positive lens unit L4 required to change the diopter is small as compared with the focal distance of the lens L4, the value of y changes very slightly with the change of x. It is evident that the magnification of the target image is little changed by moving the third lens unit L4.

In the above explanation of the image height, the composite system of the negative lens unit L2 and the second positive lens unit L3 has been regarded as a single lens group to establish the correspondence between the apparatus according to the invention and the apparatus disclosed in the above-referred U.S. patent. However, it is to be understood that the provision of the negative lens unit L2 in addition to the second positive lens unit L3 according to the invention brings forth particular advantages. By additionally providing the negative lens unit on the eye side of the second positive lens it is possible to position the principal plane of the lenses as a composite system at a position on the side of the third positive lens unit L4, thereby providing a wider moving range for the third positive lens unit L4. Thus, a substantial broadening of the diopter correction range has been obtained according to the invention.

In the construction of the eye examination apparatus shown in FIG. 1, the astigmatic system C1, C2 has been disposed approximately conjugate with the imaginary spectacles (Lo) wearing position Q for the examined eye E relative to the first positive lens unit L1. Usually the position Q is 12-14 mm distant from the cornea of the examined eye E. Regarding the examined eye, this arrangement is optically equivalent to an arrangement of a cylindrical lens at the position Q instead of the cylindrical lenses C1 and C2 in FIG. 1. Therefore, between the composite astigmatic degree of the two cylindrical lenses and the astigmatic degree of the whole optical system of the apparatus there is held a linear relationship, which enables the eye examination to be performed accurately and promptly.

It is to be understood that within the scope of the invention various modifications and changes are possible in the above-shown embodiment. The lenses which constitute the astigmatic system in the apparatus are not limited to cylindrical lenses only as shown in the figures but astigmatic lenses also may be used to correct the degree and axis of astigmatism. While the cylindrical lenses C1 and C2 have been disposed on the eye side of the lens L2 in the embodiment shown in FIG. 1, it is obvious that the cylindrical lenses C1 and C2 may be disposed on the target side of the lens L2 without any substantial change of effect.

As readily understood from the foregoing, the present invention provides a subjective eye-examining apparatus which is simple in construction and can be used almost anywhere without limitation because the target mark is contained in the apparatus itself. The apparatus according to the invention has many advantages over the prior art. Since the correction of diopter can be made in the manner of the so-called internal focusing system by moving the third positive lens unit, it is unnecessary for the target to be moved along the optical axis. When a set of target marks is used and changed from one to another in the manner of turret, it is only necessary to rotate the turret. Therefore, also in this case, it is possible to provide a small and simple apparatus for eye examination. It is also possible to combine the subjective eye-examining apparatus according to the invention with a known automated apparatus for objective eye examination. With such a combination, the subject eye can be examined at first for any abnormality of refractive power by the automatic objective examination apparatus, the value found by the automatic apparatus can be input into the subjective eye-examining apparatus according to the invention and then the eye can be further examined by the latter apparatus to measure the corrected sight, after correction of the previously found abnormality of eye refractive power and/or to measure the refractive power more precisely. In this case, the optical system of the subjective eye-examining apparatus according to the invention may be used also for the eye fixation mark optical system of the objective eye-examining apparatus in common.

I claim:

1. An eye examining apparatus for examining the eye of an examinee by letting the examinee look at a target with an examined eye in a specified position to determine the optical characteristics of spectacles needed by the examinee, said apparatus comprising:
    (a) a first positive lens unit:
    (b) a negative lens unit;
    (c) a second positive lens unit;
    (d) a third positive lens unit movable along an optical axis, said first positive lens unit, negative lens unit, second positive lens unit and third positive lens unit being arranged between the examined eye and the target in the named order from the side of the examined eye, the focal point on the eye side of the composite system composed of said negative lens unit and said second and third positive lens units being approximately coincident with the position conjugated with the pupil of the examined eye relative to said first positive lens unit; and
    (e) an astigmatic system disposed approximately conjugate, relative to said first positive lens unit, with the position at which spectacles should be located if the examinee wore the spectacles with the examined eye being in said specified position, said astigmatic system including two astigmatic lenses rotatable about the optical axis, one of said two astigmatic lenses being a positive cylindrical lens and the other of said two astigmatic lenses being a negative cylindrical lens, and wherein said negative lens unit and said second and third positive lens units form an image of the target at a position in the vicinity of the focal point on the target side of said first positive lens unit.

2. Apparatus according to claim 1, wherein said astigmatic system is disposed approximately conjugate, relative to said first positive lens unit, with a position 12-14 mm distant from said specified position toward the target side.

3. An eye examining apparatus for examining the eye of an examinee by letting the examinee look at a target with an examined eye in a specified position to determine optical characteristics of spectacles needed by the examinee, said apparatus comprising:
    (a) a first positive lens unit;
    (b) a second positive lens unit;
    (c) a third positive lens unit movable along an optical axis, said first positive lens unit, second positive lens unit and third positive lens unit being arranged between the examined eye and the target in the named order from the side of the examined eye; and
    (d) an astigmatic system disposed approximately conjugate, relative to said first positive lens unit, with the position at which spectacles should be located if the examinee wore the spectacles with the examined eye being in said specified position, said astigmatic system controlling the axis and degree of astigmatism of said apparatus.

4. An apparatus according to claim 3, which further comprises a negative lens unit disposed between said first positive lens unit and said second positive lens unit.

5. An apparatus according to claim 3, wherein said astigmatic system is disposed approximately conjugate, relative to said first positive lens unit, with a position 12-14 mm distant from said specified position toward the target side.

6. Apparatus for eye examination according to claim 3, wherein said astigmatic system comprises two astigmatic lenses rotatable about the optical axis.

7. Apparatus for eye examination according to claim 6, wherein one of the two astigmatic lenses is a positive cylindrical lens and the other is a negative cylindrical lens.

* * * * *